(12) United States Patent
Degaetano et al.

(10) Patent No.: US 10,101,287 B2
(45) Date of Patent: Oct. 16, 2018

(54) CHROMATIC WITNESS FOR THERMAL MAPPING AND CERTIFICATION OF HEAT BLANKETS

(71) Applicant: The Boeing Company, Chicago, IL (US)

(72) Inventors: Jason A. Degaetano, Chicago, IL (US); Gary E. Georgeson, Chicago, IL (US); John R. Spalding, Chicago, IL (US)

(73) Assignee: The Boeing Company, Chicago, IL (US)

( * ) Notice: Subject to any disclaimer, the term of this patent is extended or adjusted under 35 U.S.C. 154(b) by 857 days.

(21) Appl. No.: 14/555,364

(22) Filed: Nov. 26, 2014

(65) Prior Publication Data

US 2016/0146747 A1    May 26, 2016

(51) Int. Cl.

| | |
|---|---|
| *G01K 11/00* | (2006.01) |
| *G01J 5/00* | (2006.01) |
| *G01K 1/00* | (2006.01) |
| *G01N 25/00* | (2006.01) |
| *G01N 25/72* | (2006.01) |
| *B29C 73/34* | (2006.01) |
| *G01K 11/12* | (2006.01) |

(52) U.S. Cl.
CPC ............ *G01N 25/72* (2013.01); *B29C 73/34* (2013.01); *G01K 11/125* (2013.01)

(58) Field of Classification Search
USPC .............. 374/5, 7, 121, 124, 162, 141
See application file for complete search history.

(56) References Cited

U.S. PATENT DOCUMENTS

| | | | |
|---|---|---|---|
| 4,885,633 A | 12/1989 | Buck | |
| 5,756,356 A | 5/1998 | Yanagi et al. | |
| 7,246,570 B2 | 7/2007 | Weng et al. | |
| 9,446,575 B1* | 9/2016 | Georgeson | G01B 11/16 |
| 2008/0068590 A1* | 3/2008 | Martinez | G01J 5/0003 |
| | | | 356/51 |
| 2009/0036304 A1 | 2/2009 | Misner et al. | |
| 2011/0123712 A1 | 5/2011 | Becker, IV et al. | |
| 2014/0322540 A1* | 10/2014 | Ferguson | C23C 22/37 |
| | | | 428/416 |
| 2014/0328369 A1* | 11/2014 | Flinn | G01N 33/442 |
| | | | 374/57 |
| 2016/0025662 A1* | 1/2016 | Georgeson | G01N 25/72 |
| | | | 374/4 |
| 2017/0234849 A1* | 8/2017 | Flinn | G01N 33/442 |
| | | | 374/57 |

FOREIGN PATENT DOCUMENTS

| | | |
|---|---|---|
| EP | 1574832 A2 | 9/2005 |
| KR | 20110029986 A | 3/2011 |

\* cited by examiner

*Primary Examiner* — Mirellys Jagan
(74) *Attorney, Agent, or Firm* — Felix L. Fischer

(57) ABSTRACT

A method for heat blanket certification employs a thermochromatic coating containing one or more chromatic probes which is prepared and applied to a measurement surface. A test layup is created with the heat blanket and a vacuum bagging film. The vacuum bagging film is sealed and a vacuum is drawn through a vacuum probe in the vacuum bagging film. The heat blanket is brought to operating temperature and the thermochromatic coating is illuminated with ultraviolet light. The chromatic probe coloration is then observed for determination of temperature consistency in the heat blanket.

18 Claims, 5 Drawing Sheets

CHROMATIC WITNESS FOR THERMAL MAPPING AND CERTIFICATION OF HEAT BLANKETS

REFERENCE TO RELATED APPLICATIONS

This application is copending with U.S. patent application Ser. No. 13/840,980, now U.S. Pat. No. 9,372,177, entitled Method and System for Detecting Exposure of Composites to High-Temperature; Ser. No. 13/791,207, now U.S. Pat. No. 9,446,575, entitled Monitoring Composite Manufacturing and Repair Processes Using Chromatic Films; Ser. No. 14/259,519, now U.S. Pat. No. 9,970,833, entitled Witness Material and Method for Monitoring the Environmental History of an Object; and, Ser. No. 14/337,622 entitled Systems and Methods of Monitoring a Thermal Protection System, all having a common assignee with the present application, the disclosures of which are incorporated herein by reference.

BACKGROUND INFORMATION

Field

Embodiments of the disclosure relate generally to the field of certification of heat blankets and more particularly to use of a thermochromatic coating of chromatic probes applied to a witness sheet, operative surface of the heat blanket or vacuum bagging film with a vacuum bagging system test layup in which the heat blanket is brought to operating temperature and activated chromatic probes are viewed under ultraviolet illumination.

Background

Heat blankets are a critical part of composite repair process for aircraft and other systems employing composite skins and structures. Heat blankets are applied to the surface of a repair area to provide the heat needed to cure the resin system in pre-impregnated ply stack-ups. It is essential that the thermal properties of the heat blankets are controlled and consistent across the entire area of the blanket. To assure even and repeatable curing processes. To certify and monitor the performance of heat blankets, it is currently required that a thermal camera or pyrometer be used to take images of the heat blanket vacuum-bagged to a silicon pad, while the power is turned on to the blanket. Many blankets fail due to very small hot spots showing up in large view IR images, resulting in significant cost and time expenditure. To avoid failing the heat blankets, by these potentially erroneous thermal outliers, small (2" by 2") view images are taken and averaged to provide a reliable certification process. With either the IR camera or the pyrometer, moving and aiming the sensor to produce the necessary small view grid pattern is time consuming and labor intensive.

It is therefore desirable to provide a system and method for certification of heat blankets which alleviates the shortcomings of the existing methods.

SUMMARY

Embodiments disclosed herein provide a method for heat blanket certification wherein a thermochromatic coating containing one or more chromatic probes is prepared and applied to a measurement surface. A test layup is created with the heat blanket and a vacuum bagging film. The vacuum bagging film is sealed and a vacuum is drawn through a vacuum probe in the vacuum bagging film. The heat blanket is brought to operating temperature and the thermochromatic coating is illuminated with ultraviolet light. The chromatic probe coloration is then observed for determination of temperature consistency in the heat blanket.

An apparatus for performing the method of certification of heat blankets incorporates a coating containing at least one chromatic probe applied to a measurement surface. The chromatic probe is activated at a predetermined temperature. A vacuum bagging system encloses a heat blanket with an operative surface of the heat blanket adjacent and operatively engaged to the measurement surface. The heat blanket is operable within the vacuum bagging system. An ultraviolet light source illuminates the operative surface after operation of the heat blanket.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide an apparatus and method for qualifying heat blankets used for composites repairs by providing a thermal map of the active surface of the blanket. The performance of a blanket over time may be verified to assist in the decision to remove the blanket from service. A thermochromatic coating is provided on a witness sheet between the heat blanket and vacuum bag, or the vacuum bag itself, or applied directly to a side of the heat blanket. The blanket is then brought up to the temperature use value. The thermal map of the blanket created in the thermochromatic coating can be viewed under a UV light as variations in color due to thermal activation of chromatic material. Imaging with a video or still camera under UV lighting may be employed to document and certify results. Variations in the thermal profile across the blanket are compared to a preestablished allowable range. Software may be employed to overlay a 2 inch grid onto the image and automatically average and quantify and display the results for each square, and show any out of tolerance areas.

Figure 1A:
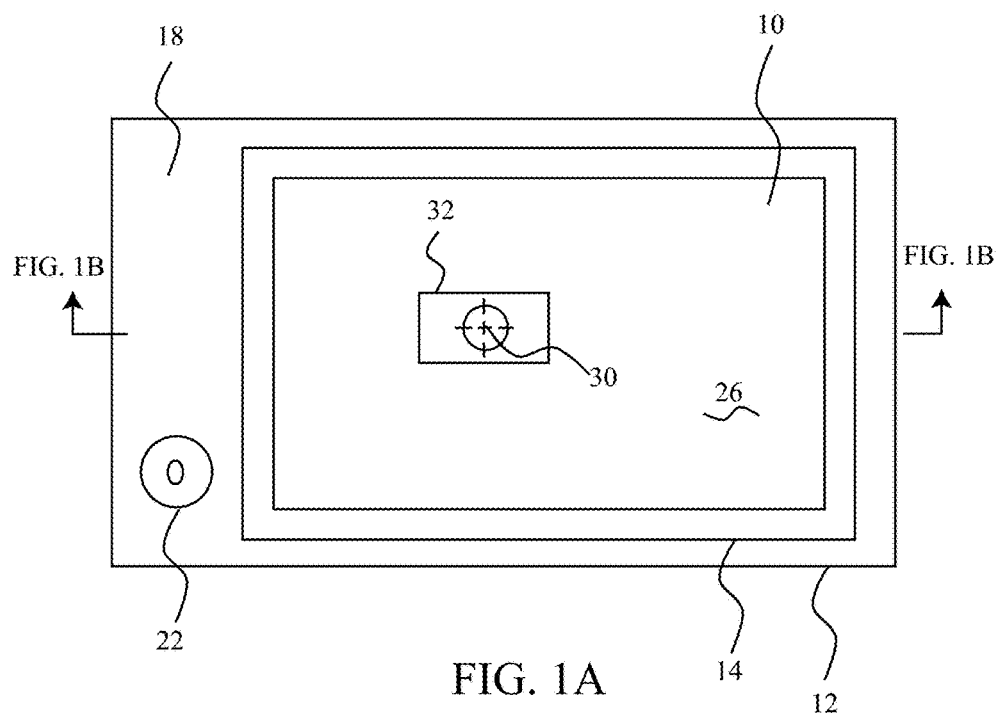
FIG. 1A is a top view of the test apparatus.
Figure 1B:
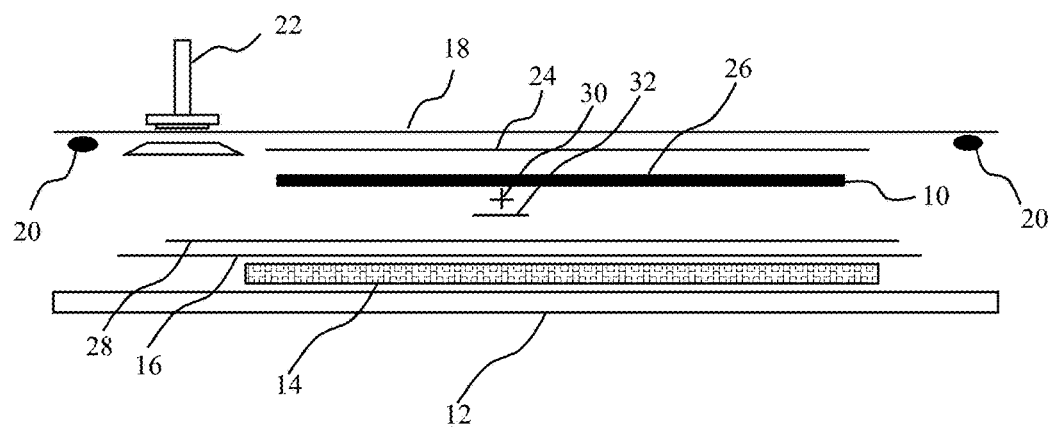
FIG. 1B is aside exploded view of the test apparatus.

Referring to the drawings, FIGS. 1A and 1B show the elements of the measurement apparatus for preforming the certification method herein. A heat blanket 10, which is to be measured or certified, is placed within a vacuum bagging system. A caul plate 12 is provided as abase and a rubber pad 14 is placed between the caul plate and heat blanket. A fiberglass breather 16 is placed between the rubber pad and heat blanket to remove any entrapped air between the rubber pad and heat blanket. A vacuum bagging film 18 is employed to encapsulate the layup. In exemplary embodiments, the rubber pad is a minimum of 0.5" thick and extends at least 1" beyond the peripheral edges of the heat blanket 10. The fiberglass breather may be one ply of 7781 fiberglass insulation cloth. The vacuum bagging film 18 is provided with appropriate edge seals 20 for sealing to the caul plate 12 and a vacuum probe 22 to draw vacuum on the bagged system. A thermochromatic witness sheet 24 may be provided, which may also be a FEP release film to prevent the vacuum bagging film 18 from adhering to the heat blanket 10. Alternatively, a thermochromatic coating may be applied directly to the surface 26 of the heat blanket or to the vacuum bagging film 18. A second FEP release film 28 may also be provided between the heat blanket 10 and fiberglass insulation cloth 16 to prevent adhering of the heat blanket to the fiberglass. For process monitoring/verification, a thermocouple 30 may be held in contact with the heat blanket 10 using high temperature adhesive tape 32 or similar means.

Figure 2:
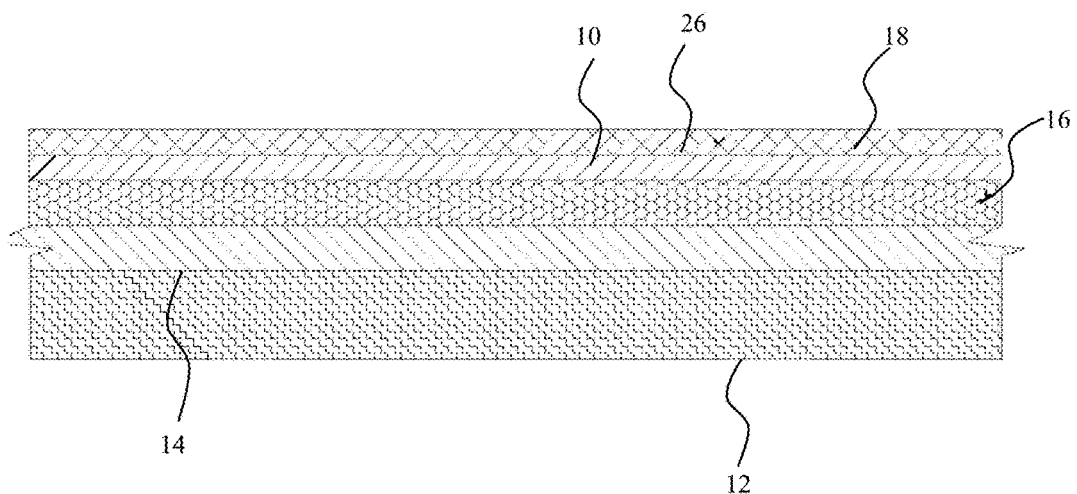
FIG. 2 is a detailed partial section view of the layers of the test apparatus.

FIG. 2 shows the layers of the heat blanket 10 and vacuum bagging system elements in close contact with vacuum applied. The heating surface 26 of the heat blanket is the desired measurement point as the operative surface and as previously described, the thermochromatic coating may be applied directly to that surface, applied to the interfacing surface of the vacuum bagging film 18 or to a witness sheet 24 as seen in FIG. 1B as a measurement surface. The thermochromatic coating incorporates at least one thermal probe (chromatic witness material reacting or activating at a particular temperature or temperature range) which changes color when activated and viewed under ultraviolet illumination. While ultraviolet illumination is used for the exemplary chromatic probes herein, in alternative embodiments chromatic probe activation may be viewed employing alternative wavelengths or wave bands of illuminating radiation. Multiple probes may be provided in the coating to sense differing temperature ranges and may provide response based on a ratio of activation or different reaction times. The multiple probes may also test uniformity of temperature on the blanket over various ranges. An example chromatic witness material for use as a thermal probe within the thermochromatic coating is AJNDE35 synthesized by the University of Washington that activates above 400 F. This probe has a time-temperature response that is well-defined. The chromatic shift in frequency (color) can be correlated to a temperature value for a selected test time. The probe material is simply mixed into the coating, which is sprayed or brushed onto the surface.

Figure 3:
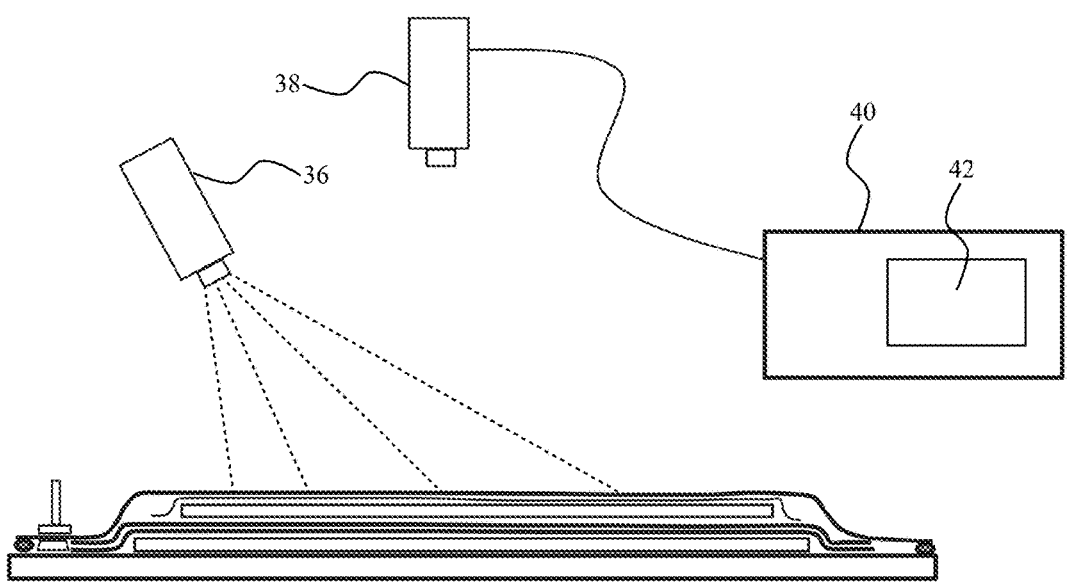
FIG. 3 is a block diagram of the elements of the test apparatus and measurement components.

The measurement components for testing of the heat blanket 10 are shown in FIG. 3. After heating of the heat blanket 10 to operational temperature, an ultraviolet light source 36 illuminates the vacuum bagged heat blanket 10 with the thermochromatic coating present in the witness sheet 24, on the heat blanket surface 26 or the vacuum bagging film 18. The resulting color emissions from the thermochromatic coating may be visually evaluated and may also be recorded by a still or video camera 38. Output from the camera 38 may be input to a computer 40 to record the data. The computer may include operative elements to provide further analysis including overlaying a grid pattern onto the resulting images with color analysis of the individual grid elements to determine uniformity of heating of the blanket and actual temperatures achieved by the heat blanket in each grid element. A display 42 may provide an output from the computer for viewing by an operator. Certain chromatic probes may provide a persistent color change once activated by reaching temperature. For such probes, the ultraviolet illumination may be accomplished on the witness sheet, heat blanket surface or vacuum bagging film after the blanket heating has been conducted and the vacuum bagging system disassembled. To be removeable, the probes may be mixed into a coating sprayed onto an adhesive-backed sheet that is applied to the heat blanket and removed after completion of the desired testing by peeling it off. A witness sheet with non-reversing temperature probes could be retained as a quality record. Witness sheets with reversing temperature probes could be used and reused and the camera images of the witness sheets showing the color change may be preserved as the quality record.

Figure 4:
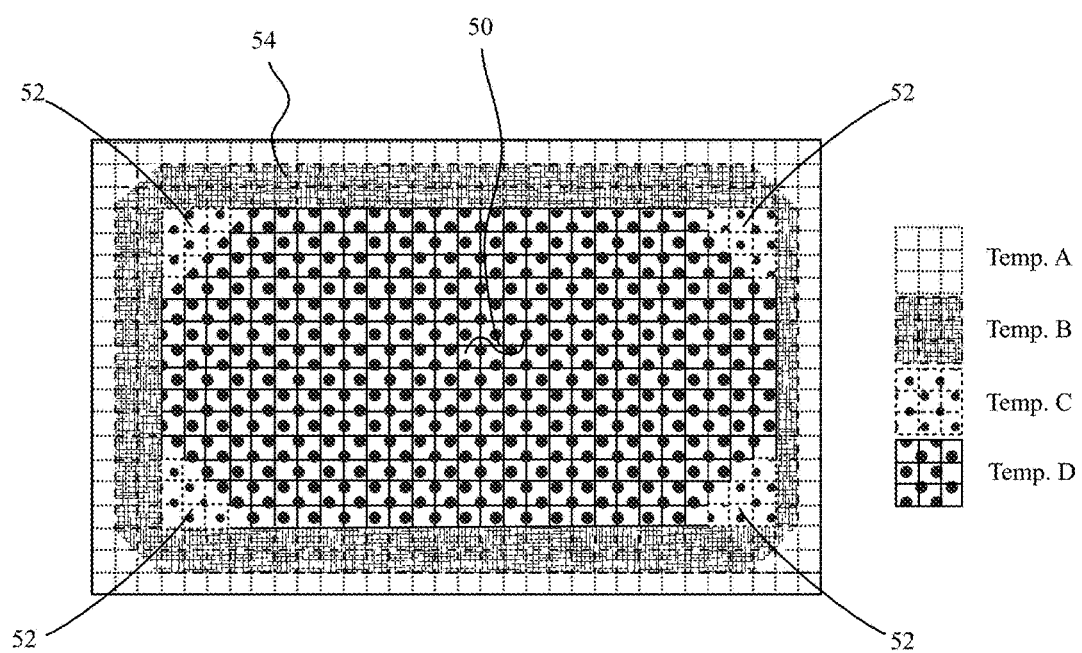
FIG. 4 is a representative view of the thermochromatic representation of the thermal profile of the heat blanket as measured; and, FIG. 5 is a flowchart showing the method for testing of a heat blanket using a thermochromatic witness coating.

An example of test results display is shown in FIG. 4. In the example, the desired heat blanket temperature is 350 F. 350 F is a typical heat blanket requirement because of the resins often used. In alternative embodiments for lower temperature curing composites, 250 F might be used, or with high temperature thermoplastics, 700 F might be used. The chromatic probe calibrated for activation at that temperature shows an even coverage area 50 over substantially the entire heat blanket except for corner elements 52. The areas outside the area of the blanket show no activation by the 350 F chromatic probe (but may show a different coloration by a second chromatic probe at lower temperature in regions 54 outside the area of the heat blanket. If any portion of the heat blanket failed to achieve the required temperature, a visual area would be present where the 350 F chromatic probe had not been activated. Similarly, a higher temperature chromatic probe may also be present in the coating which would indicate areas of over-temperature on the heat blanket area. The computer analysis may further elucidate the results by providing coloration of the grid elements in the display to show the calculated chromatic probe values within the grid elements.

Figure 5:
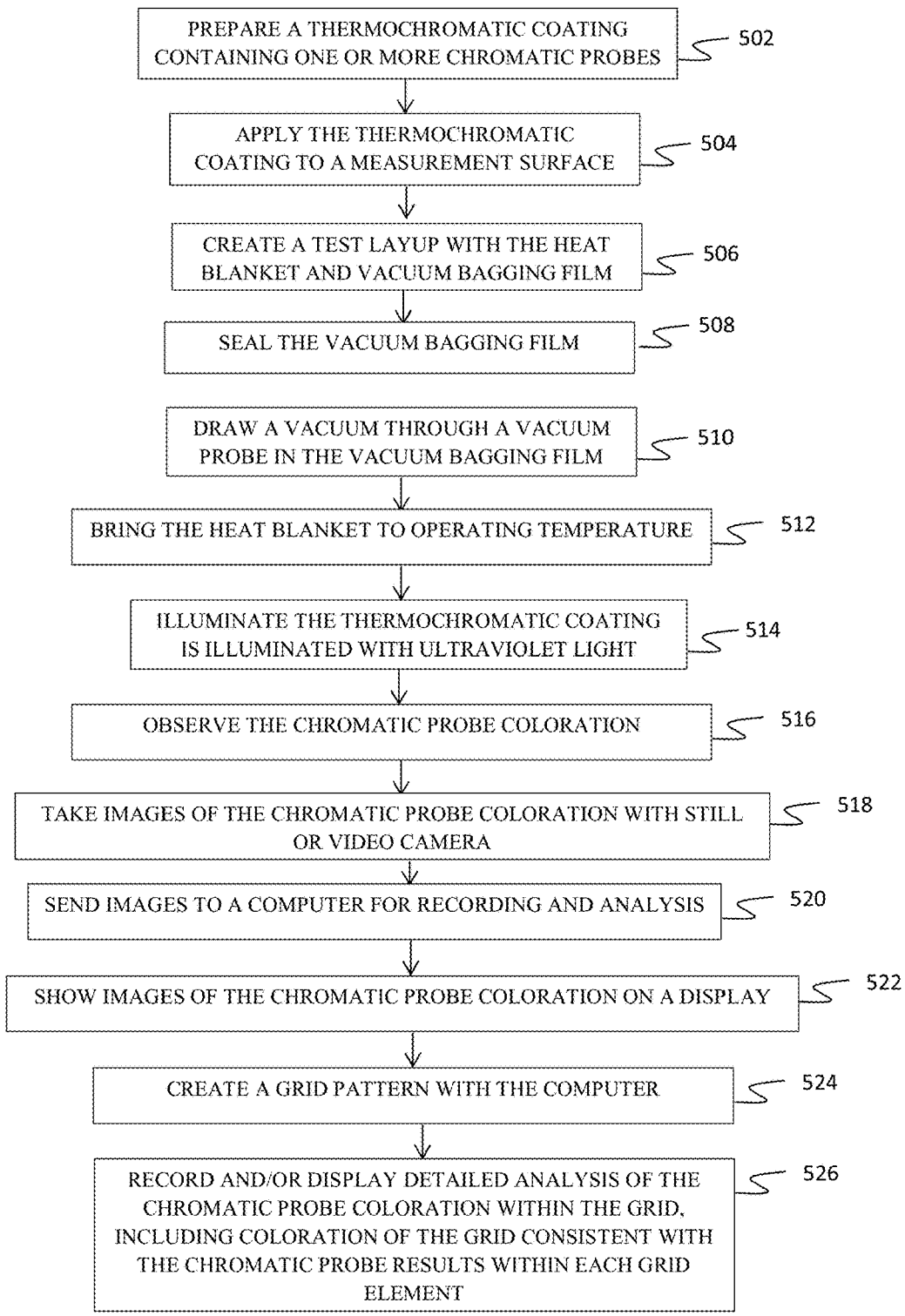

The embodiments described provide a method for testing or certification of heat blankets as shown in FIG. 5. A thermochromatic coating containing one or more chromatic probes is prepared, step 502. The thermochromatic coating is applied to a measurement surface, step 504, which may be the operative surface of the heat blanket, a witness sheet to be placed adjacent the operative surface, or the vacuum bagging film employed for testing of the heat blanket. A test layup is created, step 506, which may employ certain of the following components, a caul plate, a rubber pad, a fiberglass cloth breather, the heat blanket and the vacuum bagging film (with optional FEP release films between the fiberglass breather and heat blanket and between the heat blanket and vacuum bagging film) with the witness sheet, if employed, placed intermediate the heat blanket and vacuum bagging film. The vacuum bagging film is sealed to the caul plate, step 508, and a vacuum is drawn through a vacuum probe in the vacuum bagging film, step 510. The heat blanket is then brought to operating temperature, step 512. The thermochromatic coating is illuminated with ultraviolet light, step 514, and the chromatic probe coloration is observed, step 516. Images of the chromatic probe coloration may be taken with still or video camera, step 518 and may be sent to a computer for recording and further analysis, step 520. The images of the chromatic probe coloration may be shown on a display, step 522, and the computer may create a grid pattern, step 524, and record and/or display detailed analysis of the chromatic probe coloration within the grid, including coloration of the grid consistent with the chromatic probe results within each grid element, step 526.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. A method for certification of a heat blanket comprising:
preparing a thermochromatic coating containing one or more chromatic probes;
applying the thermochromatic coating to a sheet as a measurement surface where an operative surface of the heat blanket is adjacent to and operatively engaged to the measurement surface;
creating a test layup with the heat blanket and a vacuum bagging film;
sealing the vacuum bagging film;
drawing a vacuum through a vacuum probe in the vacuum bagging film;
bringing the heat blanket to operating temperature;
illuminating the measurement surface having the thermochromatic coating with ultraviolet light; and,
observing the chromatic probe coloration.

2. The method for certification of a heat blanket as defined in claim 1 wherein creating the test layup further includes inserting selections from the set of a caul plate, a rubber pad and a fiberglass cloth breather into the test layup.

3. The method for certification of a heat blanket as defined in claim 2 wherein creating the test layup further comprises inserting FEP release films between the fiberglass breather and heat blanket and between the heat blanket and vacuum bagging film.

4. The method for certification of a heat blanket as defined in claim 1 further comprising taking images of the chromatic probe coloration with a still or video camera.

5. The method for certification of a heat blanket as defined in claim 4 further comprising sending the images to a computer for recording and further analysis.

6. The method for certification of a heat blanket as defined in claim 5 further comprising showing the images of the chromatic probe coloration on a display.

7. The method for certification of a heat blanket as defined in claim 6 further comprising creating a grid pattern with the computer and recording and displaying a detailed analysis of the chromatic probe coloration within the grid.

8. The method for certification of a heat blanket as defined in claim 7 further comprising coloring the grid consistent with the chromatic probe results within each grid element.

9. An apparatus for certification of a heat blanket comprising:
a coating containing at least one chromatic probe applied to a sheet as a measurement surface where an operative surface of the heat blanket is adjacent to and operatively engaged to the measurement surface, said chromatic probe activated at a predetermined temperature;
a vacuum bagging system incorporating a vacuum bag to enclose the heat blanket with an operative surface of the heat blanket adjacent and operatively engaged to the vacuum bag, said heat blanket operable within the vacuum bagging system; and,
an ultraviolet light source illuminating the measurement surface after operation of the heat blanket.

10. The apparatus for certification of a heat blanket as defined in claim 9 wherein the vacuum bagging system comprises a caul plate with the vacuum bagging film sealed to the caul plate.

11. The apparatus for certification of a heat blanket as defined in claim 10 wherein the vacuum bagging system further comprises a fiberglass breather cloth intermediate the caul plate and the heat blanket.

12. The apparatus for certification of a heat blanket as defined in claim 11 wherein the vacuum bagging system further comprises a rubber pad intermediate the fiberglass breather cloth and the caul plate.

13. The apparatus for certification of a heat blanket as defined in claim 9 further comprising a still or video camera adapted to record images of the measurement surface under ultraviolet illumination.

14. The apparatus for certification of a heat blanket as defined in claim 13 further comprising a computer receiving the images from the camera and displaying the images.

15. The apparatus for certification of a heat blanket as defined in claim 14 wherein the computer incorporates an operative element overlaying a grid pattern on the images.

16. The apparatus for certification of a heat blanket as defined in claim 15 wherein the computer further incorporates an operative element coloring the grid consistent with the chromatic probe coloration within each grid element.

17. A method for certification of a heat blanket comprising:
preparing a thermochromatic coating containing one or more chromatic probes;
applying the thermochromatic coating to a sheet as a measurement surface comprising one of an operative surface of the heat blanket, a witness sheet or a vacuum bagging film;
creating a test layup with the heat blanket and the vacuum bagging film;
sealing the vacuum bagging film;
drawing a vacuum through a vacuum probe in the vacuum bagging film;
bringing the heat blanket to an operating temperature;
illuminating the measurement surface having the thermochromatic coating with ultraviolet light; and,
taking images of the chromatic probe coloration with a still or video camera;
sending the images to a computer for recording; and,
creating a grid pattern with the computer and displaying a detailed analysis of coloration of the chromatic probes by coloring the grid consistent with the chromatic probe results within each grid element.

18. The method for certification of a heat blanket as defined in claim 17 wherein the measurement surface comprises the witness sheet and the step of creating a test layup further comprises placing the witness sheet adjacent an operative surface of the heat blanket.

* * * * *